United States Patent
Legrandjacques et al.

(10) Patent No.: US 6,343,874 B1
(45) Date of Patent: Feb. 5, 2002

(54) METHOD FOR THE INSPECTION OF A PART BY THERMAL IMAGING

(75) Inventors: Laurent Legrandjacques, Dijon; Christophe Dehan, Le Mans; Jean-Claude Krapez, Chatillon; Francois Le Poutre, Janvry, all of (FR)

(73) Assignees: Framatome, Courbevoie; Office National d'Etudes et de Recherches Aérospatiales "ONERA", Chatillon, both of (FR)

(*) Notice: Subject to any disclaimer, the term of this patent is extended or adjusted under 35 U.S.C. 154(b) by 0 days.

(21) Appl. No.: 09/380,498
(22) PCT Filed: Mar. 4, 1998
(86) PCT No.: PCT/FR98/00430
   § 371 Date: Jan. 27, 2000
   § 102(e) Date: Jan. 27, 2000
(87) PCT Pub. No.: WO98/39641
   PCT Pub. Date: Sep. 11, 1998

(30) Foreign Application Priority Data

Mar. 5, 1997 (FR) .............................. 97 02622

(51) Int. Cl.⁷ .................. G01N 25/72; G01J 5/00
(52) U.S. Cl. ................. 374/5; 374/4; 250/341.6; 250/332; 250/334
(58) Field of Search ................... 374/4–7, 18, 22, 374/29, 30, 161, 57, 45, 124, 137; 250/341.6, 332, 334

(56) References Cited

U.S. PATENT DOCUMENTS

| | | | | | |
|---|---|---|---|---|---|
| 3,808,439 A | * | 4/1974 | Renius | ................. | 250/334 |
| 3,842,277 A | * | 10/1974 | Jayachandra | .......... | 250/338 |
| 3,949,225 A | * | 4/1976 | Aguilera | ................. | 250/334 |
| 4,080,532 A | * | 3/1978 | Hopper | ................. | 250/332 |
| 4,429,330 A | * | 1/1984 | Chapman | ................. | 358/113 |
| 4,703,179 A | * | 10/1987 | Motooka | ................. | 250/334 |
| 4,792,681 A | * | 12/1988 | Hanson | ................. | 250/338.2 |
| 4,792,683 A | * | 12/1988 | Chang et al. | ............... | 250/341 |
| 4,860,224 A | * | 8/1989 | Cashell et al. | ......... | 364/551.01 |
| 4,875,175 A | * | 10/1989 | Egee et al. | ............ | 364/551.01 |
| 4,900,367 A | * | 2/1990 | Gergis | ................. | 136/201 |
| 4,910,401 A | * | 3/1990 | Woods | ................. | 250/332 |
| 4,956,686 A | * | 9/1990 | Borrello et al. | ............... | 357/30 |
| 4,989,086 A | * | 1/1991 | Schaff et al. | ............... | 358/109 |
| 5,111,048 A | * | 5/1992 | Devitt et al. | ................ | 250/342 |
| 5,131,758 A | * | 7/1992 | Heyman et al. | ............... | 374/5 |

(List continued on next page.)

FOREIGN PATENT DOCUMENTS

| | | | | |
|---|---|---|---|---|
| GB | 2168494 | * | 6/1986 | .................... 374/5 |
| JP | 62127660 | * | 6/1986 | .................... 374/4 |

OTHER PUBLICATIONS

Non–destructive examination of fibre composite structures by thernal field techniques. McLaughlin et al. NDT iinternational.*

Primary Examiner—Diego Gutierrez
Assistant Examiner—Gail Verbitsky
(74) Attorney, Agent, or Firm—Connolly Bove Lodge & Hutz LLP.

(57) ABSTRACT

The scanning of a surface of a part is carried out by a means of imparting heat to at least one heating zone at the surface of the part. This occurs by relative displacement of the part and of the means of imparting heat. A detector is used to sense the flux radiated by the surface of the part in a detection zone displaced synchronously with the movement of the heating zone. The detector delivers, for each of the positions of a set of successive positions of the detection zone, a signal representative of the flux radiated. The scanning of the surface of the part is carried out along a determined path, in a first direction, then in a second opposite direction. For each of the successive positions of the detection zone, a differential signal is formulated.

16 Claims, 1 Drawing Sheet

U.S. PATENT DOCUMENTS

| | | | | |
|---|---|---|---|---|
| 5,246,291 A | * | 9/1993 | Lebeau et al. | 374/5 |
| 5,302,824 A | * | 4/1994 | Prager | 250/252.1 |
| 5,309,230 A | * | 5/1994 | Blondel et al. | 348/164 |
| 5,402,168 A | * | 3/1995 | Fouilloy | 348/164 |
| 5,460,451 A | * | 10/1995 | Wadman | 374/126 |
| 5,574,712 A | * | 11/1996 | Alon et al. | 369/102 |
| 5,582,485 A | * | 12/1996 | Lesniak | 374/5 |
| 5,654,977 A | * | 8/1997 | Morris | 374/4 |
| 5,667,300 A | * | 9/1997 | Mandelis et al. | 374/43 |
| 5,709,469 A | * | 1/1998 | White et al. | 374/5 |
| 5,711,603 A | * | 1/1998 | Ringermacher et al. | 374/5 |
| 5,740,272 A | * | 4/1998 | Shimada | 382/149 |
| 5,971,608 A | * | 10/1999 | Koizumi | 374/5 |
| 6,000,844 A | * | 12/1999 | Cramer et al. | 374/5 |
| 6,013,915 A | * | 1/2000 | Watkins | 250/341.1 |
| 6,049,220 A | * | 4/2000 | Borden et al. | 324/765 |
| 6,054,868 A | * | 4/2000 | Borden et al. | 324/752 |

* cited by examiner

METHOD FOR THE INSPECTION OF A PART BY THERMAL IMAGING

FIELD OF THE INVENTION

The invention relates to a method for the photothermal inspection of a part so as to detect defects or to determine characteristics of the material from which the part is made, while eliminating the disturbing effect of variations in emissivity and in absorptivity over a surface of the part on which the inspection is carried out.

BACKGROUND OF THE INVENTION

It is known to carry out the detection of planar or volume defects, of variations in materials or of thicknesses of coating layers or else to measure gradients of diffusivity or of thermal conductivity in a part by a photothermal inspection process consisting in determining the characteristics of the lateral diffusion, that is to say diffusion in a plane parallel to a surface of the part under inspection, of a thermal loading produced by local warming of the part. To do this, a warming of a zone of the surface of the part is produced and at least one detector such as an infrared detector is used to determine the rise in temperature produced by the lateral diffusion of heat imparted to the heating zone, in a detection zone situated some distance from the heating zone, on the surface of the part.

To determine the variations in the lateral diffusion in the material of the part, which are representative of the defect condition of this part or of its thermal characteristics, a scanning of the surface of the part is carried out by a means of imparting heat which can be for example a laser beam, in such a way as to displace the heating zone at the surface of the part.

The signals produced by the detector(s), during the scanning by the means of imparting heat, are representative of the rise in temperature at the surface of the part, in a detection zone whose position varies simultaneously with the position of the heating zone and which is offset by a certain distance with respect to this zone. Contactless determination of the rise in temperature in the detection zone and hence of the lateral diffusion of heat in the material and of its variations is thus carried out.

The signals produced by the detector(s) during the scanning of the part by the means of imparting heat make it possible to determine the presence of defects on or beneath the surface of the material, such as cracks or interfaces perpendicular or parallel to the surface of the part or else to determine local variations in diffusivity or in thermal conductivity at the surface or under the surface of the material.

The exploitation of the signals of the detectors by an exploitation assembly comprising, for example, a microcomputer can make it possible in particular to deliver an image of the defects situated on or under the surface of the part. The device comprising the means of imparting heat, the means of scanning the surface of the part, the detector(s) and the means of exploiting the signals of the detectors then constitutes a photothermal camera which can be used to search for or characterize defects on parts made of materials of very diverse natures.

The photothermal inspection devices known in the art use devices for imparting heat which carry out a scan of the surface of the part and a detector which is sited in such a way as to receive the thermal flux emitted by a detection zone situated some fixed distance from the heating zone and which follows the displacement of this heating zone during the scan.

The flux radiated by the surface of the material in the detection zone depends on the emissivity of the surface of the material in the detection zone and on the amount of heat imparted to the heating zone which, itself, depends on the absorptivity of the part in the heating zone.

Generally, the emissivity of the surface of the part to be inspected varies from one zone to another, that is to say varies in the course of the scanning of the part by the heat-imparting source. Likewise, the absorptivity of the material generally varies during the scanning of the part.

The measurements performed are therefore not uniquely representative of the distribution of the thermal properties of the material.

In particular, the image obtained by a photothermal camera by scanning a surface of a part is not generally representative of the defect condition of this part, owing to the disturbing effect of the variations in emissivity and in absorptivity of the part.

BRIEF DESCRIPTION OF THE INVENTION

The purpose of the invention is therefore to propose a method for the photothermal inspection of a part consisting in carrying out the scanning of a surface of the part by a means of imparting heat which imparts heat to the part, in at least one heating zone which is displaced at the surface of the part, in sensing with at least one detector the flux radiated by the surface of the part, in at least one detection zone whose position on the surface of the part varies jointly with the position of the heating zone and in formulating, by virtue of the detector, for each of the positions of a set of successive positions of the detection zone, a signal representative of the thermal flux radiated by the measurement zone, this method making it possible to eliminate the disturbing effect of variations in emissivity or in absorptivity of the part on which the inspection is carried out.

For this purpose, the scanning of the surface of the part is carried out along a determined path, in a first displacement sense, then in a second displacement sense opposite to the first, with an identical scanning rate and, for each of the successive positions of the detection zone, a differential signal is formulated by subtracting the signals obtained during the scanning in one sense and in the other of the surface of the part and the defect condition or the characteristics of the material of the part are determined on the basis of the differential signals obtained.

To provide a better understanding of the invention, the implementation of the method of photothermal inspection according to the invention will now be described, by way of non-limiting example, while referring to the appended figures, in particular in respect of the detecting of defects such as cracks in a part.

DETAILED DESCRIPTION OF THE INVENTION

Figure 1:
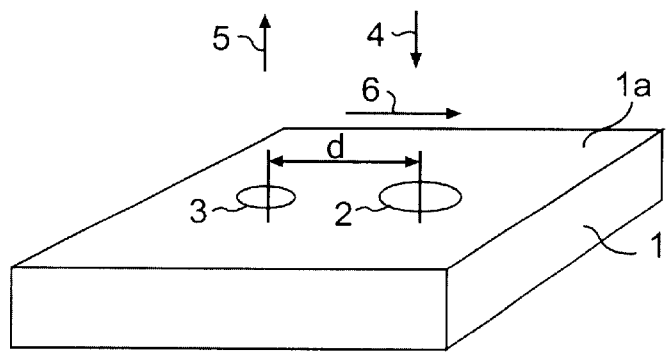
FIG. 1 is a perspective view illustrating the principle of the method of photothermal inspection to which the invention applies.

In FIG. 1 may be seen the part 1 made of the material, on which the photothermal inspection is carried out. The part has been represented in the shape of a right-angled parallelepiped and the surface 1a on which are carried out the scan by the means of imparting heat and the measurement of thermal flux, by a plane face of the right-angled parallelepiped. Of course, the part could have any shape other than the shape of a right-angled parallelepiped and the scanned surface could be a different surface from a plane surface.

On the surface 1a of the part 1 under photothermal inspection, a zone 2 of the surface 1a has been represented arbitrarily in the shape of a circular zone, in which heat is imparted to the part 1 made of the material.

Likewise, the detection zone in which the thermal flux radiated by the part 1 is detected has been represented arbitrarily in the shape of a circular zone 3.

The imparting of heat to the zone 2 is shown schematically by the arrow 4 and the detecting of the thermal flux radiated by the zone 3, by the arrow 5.

The zones 2 and 3 are spaced apart on the surface 1a of the part 1, the distance of spacing d having been represented in FIG. 1.

The scanning of the surface 1a of the part 1 by the means of imparting heat and by the axis of aim of the detector has been shown schematically by the arrow 6.

The detection zone 3 transmits the temperature rise information, for example the radiated thermal flux, to an infrared detector.

Generally, in the known devices of the prior art, the distance d between the heating zone and the measurement zone is constant during the scan, the radiated flux or the rise in temperature being measured at a fixed distance from the heating zone moving on the surface of the part. The position of the measurement zone is deduced at each instant from the position of the heating zone by a constant vector translation in any direction with regard to the displacement.

Figure 2:
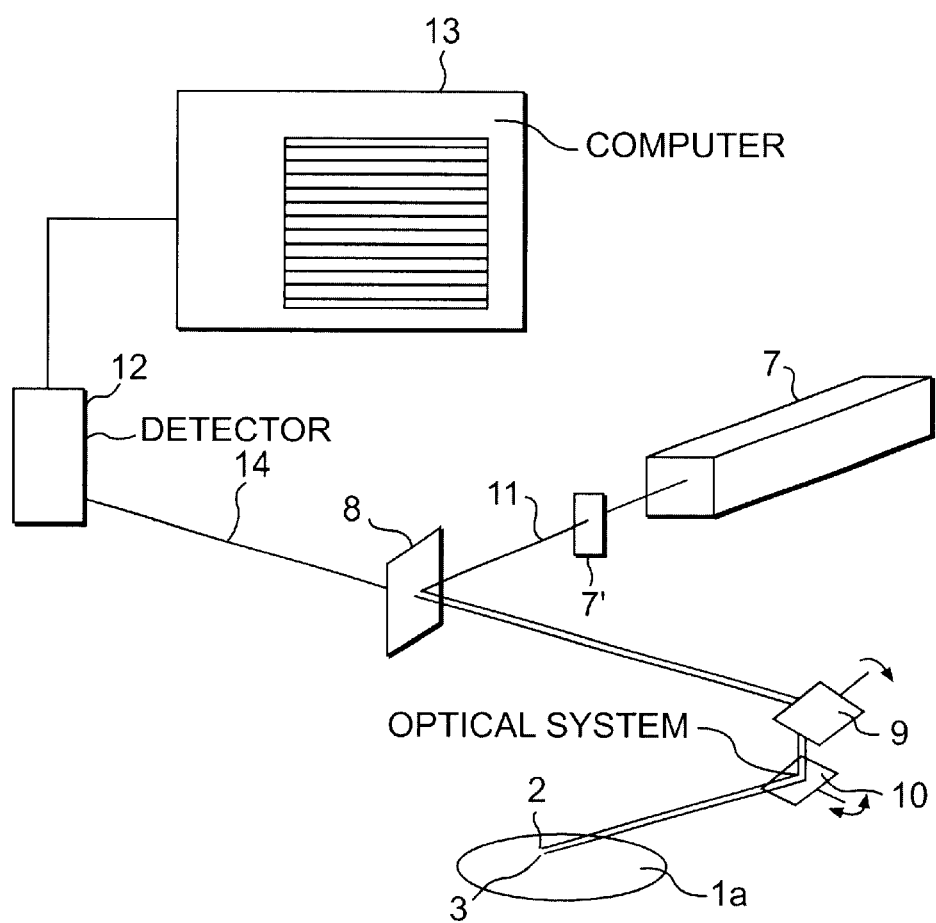
FIG. 2 is a schematic view of an exemplary device for implementing the method of photothermal inspection.

Represented by way of example in FIG. 2 is a measurement device making it possible to carry out the photothermal inspection of a sample, part of the surface 1a of which has been represented.

The device includes a laser source 7, a device 7' for adapting the spatial distribution of the laser flux and optical means consisting of mirrors 8, 9, 10 making it possible to transmit the laser beam 11 to the surface 1a of the part so as to carry out the heating in a heating zone 2.

The flux radiated in a measurement zone 3 is transmitted by the mirrors of the optical system 10, 9 to a detector 12 linked to a computer 13 for processing the signals delivered by the detector.

The mirrors 9, 10 of the optical assembly make it possible to perform a scan of the surface 1a of the sample with the laser beam 11 and simultaneously to transmit to the detector 12 the flux radiated in a measurement zone 3 of the surface 1a of the sample, situated a fixed distance from the heating zone 2.

In general, use is made of a continuous-wave laser, the spatial distribution of whose beam 11 is adapted to the measurement envisaged; thereafter, the beam of the laser is focused onto the surface of the sample. It is sometimes preferable to use a beam whose intensity is modulated over time. The infrared detector is a detector which is sensitive in a range of wavelengths whose band lies between 0.4 to 20 $\mu$m. The mirrors 9 and 10 are motorized steerable mirrors which are displaced in such a way as to carry out a complete line-by-line scan of the surface 1a of the sample. The optical paths of the laser excitation beam 11 and of the radiated flux 14 are colinear up to the semireflecting mirror 8.

The thermal flux radiated by the measurement zone 3 depends on the local emissivity $\epsilon$ of the surface 1a of the sample. This emissivity can vary from 0 to 1 as a function of the local features of the surface portion constituting the measurement zone at a given instant.

In the case of optical type heating, for example by a laser source or an incandescent lamp, the effectiveness of the heating depends on the coefficient of absorptivity a of the portion 2 of the surface which is heated at a given instant, this coefficient of absorptivity varying from 0 to 1. If the incident power of the excitation source 7 is $P_0$, the power actually transmitted to the material, for a given position of the heating zone, is $\alpha P_0$.

A Cartesian reference frame consisting of a system of axes Ox, Oy is used to pinpoint the position of the points of the surface 1a of the sample.

$\Delta T(x,y)$ denotes the rise in temperature in the detection zone 3 with coordinates x and y and $S(x,y)$ denotes the signal received by the detector. If Ox is the direction of scan, the rise in temperature $\Delta T(x,y)$ depends on the temperature rises $\Delta T(x-a,y)$ generated by the heating system at the positions x-a reached by the system along the scanning path, that is to say for a varying from x to 0.

It can be shown that the signal received by the detector depends:

on the temperature rise $\Delta T(x,y)$ caused by the heating in the detection zone and by the variations in diffusivity existing in the neighborhood of the heating zone 2 and detection zone 3. (It should be noted that $\Delta T$ depends on the rate and on the sense of scanning and on the relative arrangement of the heating 2 and detection 3 zones)

on the local optical characteristics of the surface to be examined (E over the detection zone 3 and $\alpha$ over the heating zone 2).

In the case where the variations in the optical characteristics at the surface 1a of the part 1 are not negligible, the signal variations observed may be considerable and may represent almost exclusively the variations in the optical characteristics rather than representing the variations in diffusivity which one seeks to determine.

The method according to the invention makes it possible to eliminate the disturbing effect of the variation in the optical characteristics of the surface of the part inspected and to obtain the thermal characteristics of the part directly by exploiting the signals of the detectors; on the basis of these characteristics, it is then possible to detect and locate defects or else determine diverse characteristics of the material of the part.

It should be noted that the method according to the invention applies regardless of the type of detection used; it applies equally well when using a detector in the near infrared, in the visible and in the ultraviolet; it can also be applied in respect of other detection in the field of thermoreflectivity.

The method according to the invention consists in carrying out the scanning of the surface of the part, that is to say the displacing of the heating zone 2 and of the detection zone 3, along a determined path, initially in a first displacement sense, then in a second displacement sense opposite to the first with an identical scanning rate.

For example, in the case where the scanning of the surface 1a of the part 1 is carried out along a succession of mutually parallel lines whose direction is the direction of the arrow 6, a scan in a first sense (for example the sense of the arrow 6) and a scan along the same line in the opposite sense and with the same rate as during the scan in the first sense are carried out for each of the scan lines.

In the course of the scan in the first displacement sense, along a scan line, successive signals representative of the flux radiated by the detection zone 3 in successive positions along the scan line are captured at the output of the detector 12. During the scan of the same line in the second displacement sense, successive signals are captured at the output of the detector 12 which are representative of the thermal flux radiated by the detection zone 3 in successive positions which correspond to the detection zone positions in which measurement signals were captured during the scan in the first displacement sense. The measurement signals representative of the flux radiated by the measurement zone 3 in each of the successive positions while scanning in one sense and in the other are stored in the memory of the computer 13.

By subtracting the signals, so as to obtain in each case a differential signal for each of the positions of the measurement zone 3, the disturbing effect of the optical characteristics of the surface of the part, due to the variations in the emissivity factor and in the absorptivity factor, along the surface of the part, is eliminated.

Specifically, generally $\Delta T(x,y)$ depends on the scan sense.

However, the difference in temperature rise hen the scan sense is reversed may become small or even zero when presented only with optical defects of the surface. In this case, $\Delta S(x,y)$ equals zero.

Conversely, in the case of a thermal diffusivity gradient, for example due to defects of the material such as cracks, the difference in temperature rise $\Delta(\Delta T(x,y))$, is different from zero.

In this case, $\Delta S(x,y)$ is different from zero; a measurable differential signal is therefore obtained.

By determining, for each of the positions of the detection zone, the differential signal $\Delta S(x,y)$ between the signal obtained in one scan sense and the signal obtained in the opposite sense, the influence of the optical characteristics of the surface of the part on the measurement signal is therefore eliminated.

The differential signals are therefore properly representative of the thermal characteristics of the material.

In the case where a nondestructive test is carried out on the part by photothermal inspection, a first image of the surface of the part is produced from the signals output by the detector during the scanning of the part along a certain path in a first scan sense, then a second image is produced from the signals delivered by the detector while scanning the surface of the part along the same path but with an opposite scan sense. Thereafter a pointwise subtraction of the two images is carried out so as to create a third image ridded of the information related solely to the surface optical properties of the part examined.

The scanning of the surface of the part can be carried out with any path, for example consisting of parallel lines joined up at their ends so as to constitute a path having a notchlike shape or a comblike shape.

The acquisition of the measurements corresponding to the images in the first sense, or outward sense of the scan, or in the second sense, or return sense of the scan, can be successive, that is to say a complete scan of the surface is performed in the outward sense followed by a complete scan of the surface in the return sense or else quasi-simultaneously, by performing the acquisition of the signals for the first line of the scan in the outward sense and then for the first scan line in the return sense, before passing to the second line of the scan and then to each of the successive scan lines. In each case, a differential signal is determined by subtracting the measurement signals in each of the positions of the measurement zones in the outward sense and the return sense.

As a function of the nature of the materials and of the surfaces under inspection, the sign and the value of the spatial offset between the heating zone 2 and the detection zone 3 (this offset being defined by the components dx and dy of a vector whose origin is the heating zone and whose tip is the detection zone) will be retained or modified between the outward scan and the return scan so as to enhance the suppressing of the unwanted components of the signal.

In the same manner, it will be possible to modify the area, the shape or the spatial distribution (of power in respect of excitation and of sensitivity in respect of detection) of the zones 2 and 3 between the outward scan and the return scan.

Scanning being carried out along the axis Ox, the spacing dx along this axis is regarded as positive if the vector whose origin is the heating zone and whose tip is the detection zone is oriented in the sense of the displacement. The spacing dy along the axis Oy is determined by orienting the axis Oy in such a way as to pass from the axis Ox to the axis Oy by a 90° anticlockwise rotation.

A conventional liquid penetrant type nondestructive test has been performed on a metal part containing emergent cracks a few micrometers in aperture. On the print obtained, dark streaks indicate the position of the cracks.

It has been sought to compare the print with an image representative of the information obtained customarily, when employing an imaging device involving a photothermal camera, without using the method of the invention. The photothermal image is very strongly disturbed by the influence of the optical characteristics of the surface examined which is the same surface as that of the metal part on which the liquid penetrant test is performed. It is therefore difficult to pinpoint the cracks which were highlighted by the liquid penetrant method.

The print obtained, during the liquid penetrant test, has also been compared with an image obtained by a photothermal camera technique implementing the method of the invention, that is to say by carrying out a double scan and a reconstruction of the image on the basis of differential signals determined during the outward scan and the return scan, in the same zones. The image portrays only the emergent cracks of the part. The results obtained are identical to the results obtained by the liquid penetrant test, the optical characteristics of the surface examined having been eliminated.

The method according to the invention therefore makes it possible to eliminate the effect of the inhomogeneities of an optical nature of the surface under photothermal inspection and to obtain results which are perfectly representative of the variations in the thermal characteristics of the material in the neighborhood of the surface being scanned. Surface defects or those situated under the surface of the part under inspection can thus be visualized directly.

The method according to the invention applies to all devices for nondestructive testing, whether these devices are used for detecting planar defects or volume defects perpendicular or parallel to the surface, variations in material or thicknesses of layers. The method applies also to devices for characterizing zones situated on the surface or under a surface of a part, by determination of local gradients of diffusivity or of thermal conductivity.

The devices to which the method of the invention applies comprise detectors for the contactless determination of the rise in temperature due to the diffusion of a thermal disturbance produced by local warming of the material, these devices making it possible to detect or to characterize the presence of local thermal diffusivity gradients.

The devices to which the invention applies make it possible to carry out synchronous displacement, that is to say one with a constant spacing at the surface of the part of a heating zone 2 and of a detection zone 3. The displacement between the heating and detection zones at the surface of the part can be obtained either by using a fixed part on a surface of which is displaced a heating zone and a detection zone or else by using a moveable part which is displaced with respect to a fixed device for imparting heat.

The spacing between the heating zone and the detection zone can be zero, positive or negative, it being possible to choose this spacing to be for example between 0 and 10 mm.

The spacing can be modified in amplitude and in sign (along x or y) between the outward scan and the return scan so as to enhance the suppressing of the unwanted components of the signal.

The heating and detection zones 2 and 3 may have any shape and the area of these zones may be fixed at any value between two limits such as 1 $\mu m^2$ and 1000 $mm^2$. The area of the heating zone 2 can be different from the area of the detection zone.

To improve performance, it is possible to modify the area and/or the shape of the heating zone and/or of the detection zone and/or the spatial distribution of power and/or of sensitivity inside the zones 2 and 3, respectively, between the outward and return.

It is also possible to impart heat to at least two heating zones 2 and to carry out the detection of the measurement signals in a detection zone situated between the heating zones.

It is thus possible to impart heat to an annular zone and to carry out a detection of measurement signals in a detection zone situated inside the annular heating zone.

The heating of the material of the part can be continuous or modulated over time. The detection, that is to say the measurement of the temperature rises in the detection zone on the basis of the radiated flux, can be carried out continuously or synchronously with the heating if the latter is carried out in a modulated manner. In all cases, the differential signals must be obtained by subtracting two signals in identical positions of the detection zone, in the course of the outward scan and of the return scan, respectively.

The method of the invention can be applied to the nondestructive testing or to the determination of diffusivity characteristics of parts made of any material. In particular, the method of the invention is applied to the pinpointing of the emergent cracks on elements or components of a nuclear reactor, for example welded bimetallic bonds between a first element and a second element whose compositions or structures are different, especially welded bonds between a ferritic steel element and an austenitic steel element or pipework welds on which a test is to be carried out from the inside, or else thermal barriers of primary coolant pumps.

The method applies also to the pinpointing of nonemergent cracks on surfaces which have been subjected to compression by shot peening, for example exchange surfaces of a steam generator or under a protective coating having a thickness of 0.1 to 1 mm, such as the stainless steel coating of certain regions of the primary cooling circuit of a pressurized water-cooled nuclear reactor.

What is claimed is:

1. A method for the photothermal inspection of a part consisting in carrying out the scanning of a surface of the part by a means for imparting heat which imparts heat to the part, in at least one heating zone, in sensing with at least one detector the flux radiated by the surface of the part, in at least one detection zone whose position on the surface of the part varies jointly with the position of the heating zone and in formulating, by virtue of the detector, for each of a number of positions of a set of successive positions of the detection zone, a signal representative of thermal flux radiated or of a rise in temperature in the detection zone, wherein the scanning of the surface of the part is carried out along a determined path, in a first directional displacement sense, then in a second directional displacement sense opposite to the first, with an identical scanning rate and that, for each of successive positions of the detection zone, a differential signal is formulated by subtracting signals obtained during the scanning in one sense and in the other of the surface of the part and that a defect condition or characteristics of a material of the part are determined on the basis of differential signals obtained.

2. A method according to claim 1, wherein the heating zone and the detection zone are separated by a constant distance (d) on the surface of the part represented by a vector whose components in a Cartesian reference frame may be positive, negative or zero.

3. A method according to claim 2, wherein the distance (d) between the heating zone and the detection zone is between 0 and 10 mm.

4. A method according to claim 1, wherein the distance (d) of spacing between the heating zone and the detection zone is the same during the scanning, in one sense and then in an opposite sense, of the surface of the part.

5. A method according to claim 1, wherein the distance (d) of spacing between the heating zone and the detection zone varies in sign or in amplitude between the scan in the first displacement sense and the scan in the second displacement sense.

6. A method according to claim 1, wherein the individual area of the heating zone and of the detection zone is between 1 $\mu m^2$ and 1000 $mm^2$.

7. A method according to claim 6, wherein the area of the heating zone is different from the area of the detection zone.

8. A method according to claim 1, wherein an image of the surface showing defects of the material is formulated from the differential signals.

9. A method according to claim 1, wherein the scanning of the surface of the part is carried out along a path consisting of parallel lines joined up at their ends, having a notchlike or comblike shape.

10. A method according to claim 1, wherein an acquisition of the signals of the detector is carried out in the first directional displacement sense, in the course of a first complete scan of the surface of the part, then in the second directional displacement sense in the course of a second complete scan of the surface of the part.

11. A method according to claim 1, wherein an acquisition of the signals of the detector is carried out, for each of the lines of the scan, in the first sense of scan, then in the second sense of scan of the surface of the part.

12. A method according to claim 1, wherein the heating of the part and the detecting of the signals are carried out in a continuous manner.

13. A method according to claim 1, wherein the heating of the part and the detecting of the signals are carried out in a modulated manner.

14. A method according to claim 1, wherein at least one of the parameters, area of the heating zone or of the area of the detection zone, shape of the heating zone or shape of the detection zone, excitation spatial distribution of heating power, detection spatial distribution of the sensitivity of detection, is modified between the scan in the first direc tional displacement sense and the scan in the second directional displacement sense, so as to improve the differential signals.

15. A method according to claim 1, wherein heat is imparted to more than one heating zones of the surface of the part and the detecting of measurement signals is carried out in a detection zone situated between the heating zones.

16. A method according to claim 1, wherein heat is imparted to an annular heating zone of the part and the detecting of the signals is carried out in a detection zone situated inside the annular heating zone.

* * * * *